(12) United States Patent
Burbank et al.

(10) Patent No.: US 7,325,546 B2
(45) Date of Patent: Feb. 5, 2008

(54) UTERINE ARTERY OCCLUSION DEVICE WITH CERVICAL RECEPTACLE

(75) Inventors: Fred H. Burbank, Laguna Niguel, CA (US); Michael L. Jones, San Clemente, CA (US); Greig E. Altieri, Laguna Beach, CA (US); Guillermo Elizondo-Riojas, Monterrey (MX)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 435 days.

(21) Appl. No.: 10/718,222

(22) Filed: Nov. 20, 2003

(65) Prior Publication Data

US 2005/0113852 A1   May 26, 2005

(51) Int. Cl.
 *A61B 17/08* (2006.01)
 *A61B 17/42* (2006.01)
 *A61F 6/14* (2006.01)
 *A61F 6/06* (2006.01)

(52) U.S. Cl. ............... 128/836; 606/119; 606/158; 128/841

(58) Field of Classification Search ........ 606/158, 606/119; 128/836, 841
See application file for complete search history.

(56) References Cited

U.S. PATENT DOCUMENTS

| | | | |
|---|---|---|---|
| 2,400,251 A * | 5/1946 | Nagel | ............ 606/119 |
| 3,209,753 A | 10/1965 | Hawkins et al. | |
| 3,411,505 A | 11/1968 | Nobis | |
| 3,777,740 A | 12/1973 | Hokanson | |
| 3,779,248 A | 12/1973 | Karman | |
| 4,226,240 A | 10/1980 | Walker, Jr. | |
| 4,292,960 A | 10/1981 | Paglione | |
| 4,428,374 A | 1/1984 | Auburn | |
| 4,428,379 A | 1/1984 | Robbins et al. | |
| 4,509,528 A | 4/1985 | Sahota | |

(Continued)

FOREIGN PATENT DOCUMENTS

DE    195 28 440 A    2/1997

(Continued)

OTHER PUBLICATIONS

International Search Report for PCT/US2004/038111, mailed May 3, 2005.

(Continued)

*Primary Examiner*—(Jackie) Tan-Uyen Ho
*Assistant Examiner*—Melissa Ryckman

(57) ABSTRACT

An intravaginal uterine artery occlusion device is used for treating uterine disorders such as fibroids, dysfunctional uterine bleeding, postpartum hemorrhage and the like. A occlusion device has a cervical receptacle with an open distal end for receiving the patients uterine cervix, an elongated shaft having a distal end secured to the closed proximal end of the cervical receptacle, and an inner lumen extending to the distal end of the shaft. The patient's uterine cervix is held within the interior of the receptacle by the application of a vacuum to the interior of the receptacle through the inner lumen of the shaft while the leading edge(s) of the cervical receptacle press against the patient's vaginal fornix to occlude the uterine artery. A blood flow sensor may be provided on the leading edge of the receptacle to aid in locating a uterine artery and to monitor blood flow through the uterine artery.

38 Claims, 14 Drawing Sheets

U.S. PATENT DOCUMENTS

| | | |
|---|---|---|
| 4,650,466 A | 3/1987 | Luther |
| 4,757,823 A | 7/1988 | Hofmeister et al. |
| 4,945,896 A | 8/1990 | Gade |
| 4,991,588 A | 2/1991 | Pflueger et al. |
| 4,994,069 A | 2/1991 | Ritchart et al. |
| 5,037,430 A | 8/1991 | Hasson |
| 5,037,433 A | 8/1991 | Wilk et al. |
| 5,081,997 A | 1/1992 | Bosley et al. |
| 5,108,408 A | 4/1992 | Lally |
| 5,201,314 A | 4/1993 | Bosley et al. |
| 5,226,911 A | 7/1993 | Chee et al. |
| 5,261,409 A | 11/1993 | Dardel |
| 5,275,166 A | 1/1994 | Vaitekunas et al. |
| 5,289,831 A | 3/1994 | Bosley |
| 5,336,229 A | 8/1994 | Noda |
| 5,336,231 A | 8/1994 | Adair |
| 5,383,922 A | 1/1995 | Zipes et al. |
| 5,456,693 A | 10/1995 | Conston et al. |
| 5,458,596 A | 10/1995 | Lax et al. |
| 5,488,958 A | 2/1996 | Topel et al. |
| 5,496,331 A | 3/1996 | Xu et al. |
| 5,507,744 A | 4/1996 | Tay et al. |
| 5,542,944 A | 8/1996 | Bhatta |
| 5,549,624 A | 8/1996 | Mirigian et al. |
| 5,549,824 A | 8/1996 | Trumpf et al. |
| 5,556,396 A | 9/1996 | Cohen et al. |
| 5,570,692 A | 11/1996 | Morinaga |
| 5,588,960 A | 12/1996 | Edwards et al. |
| 5,598,841 A | 2/1997 | Taniji et al. |
| 5,614,204 A | 3/1997 | Cochrum |
| 5,658,299 A | 8/1997 | Hart |
| 5,662,676 A | 9/1997 | Koninckx |
| 5,662,680 A | 9/1997 | Desai |
| 5,665,096 A | 9/1997 | Yoon |
| 5,672,153 A | 9/1997 | Lax et al. |
| 5,672,172 A | 9/1997 | Zupkas |
| 5,674,243 A | 10/1997 | Hale |
| 5,691,314 A | 11/1997 | Hodgen |
| 5,697,942 A | 12/1997 | Palti |
| 5,702,407 A | 12/1997 | Kaji |
| 5,713,371 A | 2/1998 | Sherman et al. |
| 5,713,896 A | 2/1998 | Nardella |
| 5,713,942 A | 2/1998 | Stern et al. |
| 5,715,832 A | 2/1998 | Koblish et al. |
| 5,716,389 A | 2/1998 | Walinsky et al. |
| 5,720,743 A | 2/1998 | Bischof et al. |
| 5,749,879 A | 5/1998 | Middleman et al. |
| 5,759,154 A | 6/1998 | Hoyns |
| 5,766,135 A | 6/1998 | Terwilliger |
| 5,776,129 A | 7/1998 | Mersch |
| 5,792,059 A | 8/1998 | Furia et al. |
| 5,797,397 A | 8/1998 | Rosenberg |
| 5,800,378 A | 9/1998 | Edwards et al. |
| 5,817,022 A | 10/1998 | Vesely |
| 5,836,906 A | 11/1998 | Edwards |
| 5,840,033 A | 11/1998 | Takeuchi |
| 5,895,386 A | 4/1999 | Odell et al. |
| 5,895,395 A | 4/1999 | Yeung |
| 5,899,861 A | 5/1999 | Friemel et al. |
| 5,904,651 A | 5/1999 | Swanson et al. |
| 5,910,484 A | 6/1999 | Haupert, Jr. |
| 5,911,691 A | 6/1999 | Mochizuki et al. |
| 5,916,173 A | 6/1999 | Kirsner |
| 5,921,933 A | 7/1999 | Sarkis et al. |
| 5,922,008 A | 7/1999 | Gimpelson |
| 5,941,889 A | 8/1999 | Cermak |
| 5,979,453 A | 11/1999 | Savage et al. |
| 6,013,088 A | 1/2000 | Karavidas |
| 6,015,541 A | 1/2000 | Greff et al. |
| 6,019,724 A | 2/2000 | Gronningsaeter et al. |
| 6,032,673 A | 3/2000 | Savage et al. |
| 6,033,398 A | 3/2000 | Farley et al. |
| 6,034,477 A | 3/2000 | Peeters et al. |
| 6,035,238 A | 3/2000 | Ingle et al. |
| 6,039,693 A | 3/2000 | Seward et al. |
| 6,045,508 A | 4/2000 | Hossack et al. |
| 6,066,139 A | 5/2000 | Ryan et al. |
| 6,077,257 A | 6/2000 | Edwards et al. |
| 6,080,118 A | 6/2000 | Blythe |
| 6,096,051 A | 8/2000 | Kortenbach et al. |
| 6,106,473 A | 8/2000 | Violante et al. |
| 6,169,914 B1 | 1/2001 | Hovland et al. |
| 6,175,751 B1 | 1/2001 | Maizes |
| 6,186,947 B1 | 2/2001 | Ouchi |
| 6,210,330 B1 | 4/2001 | Tepper |
| 6,231,515 B1 | 5/2001 | Moore et al. |
| 6,254,601 B1 | 7/2001 | Burbank et al. |
| 6,261,234 B1 | 7/2001 | Lin |
| 6,280,441 B1 | 8/2001 | Ryan |
| 6,368,340 B2 | 4/2002 | Malecki et al. |
| 6,425,867 B1 | 7/2002 | Vaezy et al. |
| 6,905,506 B2 | 6/2005 | Burbank et al. |
| 2002/0165579 A1* | 11/2002 | Burbank et al. ............ 606/205 |
| 2002/0183771 A1 | 12/2002 | Altieri et al. |
| 2002/0188306 A1 | 12/2002 | Burbank et al. |
| 2003/0120306 A1 | 6/2003 | Burbank et al. |

FOREIGN PATENT DOCUMENTS

| | | |
|---|---|---|
| DE | 200 22 012 U1 | 5/2001 |
| EP | 0 472 368 | 2/1992 |
| EP | 0 598 579 | 5/1994 |
| EP | 0 890 342 A | 1/1999 |
| EP | 1 072 282 | 1/2001 |
| FR | 1 220 773 A | 5/1960 |
| GB | 2 302 025 | 1/1997 |
| GB | 2 302 025 A | 1/1997 |
| GB | 2 311 468 A | 1/1997 |
| SU | 1 072 859 A | 2/1984 |
| WO | WO 95/02370 | 1/1995 |
| WO | WO 95/02371 | 1/1995 |
| WO | WO 96/05776 | 2/1996 |
| WO | WO 96/10365 | 4/1996 |
| WO | WO 97/27897 | 8/1997 |
| WO | WO 97/47246 | 12/1997 |
| WO | WO 98/19713 | 5/1998 |
| WO | WO 99/00057 | 1/1999 |
| WO | WO 99/11179 A | 3/1999 |
| WO | WO 01/68720 | 9/2001 |
| WO | WO 01/80713 | 11/2001 |
| WO | WO 02/00192 | 1/2002 |
| WO | WO 02/39904 A1 | 5/2002 |
| WO | WO 02/078521 | 10/2002 |

OTHER PUBLICATIONS

Written Opinion for PCT/US2004/038111, mailed May 3, 2005.

Translation of FR 1 220 773.

Barth, Klemens H. et al., "Long Term Follow-Up of Transcatheter Embolization With Autologous Clot, Oxycel and Gelfoam in Domestic Swine", *Investigative Radiology*, May-Jun. 1977, vol. 12, pp. 273-290.

Bateman, William M.D., "Treatment of intracable menorrhagia by bilateral uterine vessel, Interruption", *Am. J. Obst. & Gynec.* 89(6):825-827 (Jul. 15, 1964).

Brigato, G. et al., "A Noninvasive Instrumental Method in Severe Postpartum Hemorrhages", *Minerva Ginecologica* 50(7-8):337-339 (1998).

Brohim, Robert M. et al., "Development of Independent Vessel Security After Ligation With Absorbable Sutures of Clips", *The American Journal of Surgery*, Mar. 1993, vol. 165, pp. 345-348.

Burbank, Fred et al., "Uterine Artery Occlusion by Embolization or Surgery for the Treatment of Fibroids: A Unifying Hypothesis- Transient Uterine Ischemia", *The Journal of the American Association of Gynecologic Laparoscopists*, Nov. 2000, vol. 7, No. 7 Supplemental, pp. S3-S49.

Fuchs, Karl, "Afibrinogenemia Treated by Ligation of Uterine Arteries", *Gynacologic* 148:407-411 (1959).

Garza Leal, J. et al., "Myoma Treatment by Transient Uterine Ischemia", *The Journal of the American Association of Gynecologic Laparoscopists* 7(3):S31 (Aug. 2000).

Hay, D.L. et al., "Hemostasis in Blood Vessels After Ligation", *Am. J. Obstet. Gynecol.*, Mar. 1989, 160:3, pp. 737-739.

Hunerbein, M. et al., "Endoscopic Ultrasound-Guided Real Time Biopsy of Peri-Intestinal Tumors", *Surgical Technology International VII*, 1998, pp. 91-95.

O'Leary, James A., M.D., "Uterine Artery Ligation in the Control of Postcesarean Hemorrhage", *The Journal of Reproductive Medicine, Inc.*, 40(3):189-193 (Mar. 1995).

O'Leary, James L., M.D. et al., "Uterine artery ligation in the control of intractable postpartum hemorrhage", Am. J. Obst. & Gynec. 94(7):920-924 (Apr. 1, 1966).

Ravina, J.H. et al., "Arterial Embolisation to Treat Uterine Myomata", *The Lancet*, Sep. 9, 1995, vol. 346, No. 8976, pp. 671-672.

Schaefer, C.J. et al., "Absorbable Ligating Clips", *Surg. Gynecol. Obstet.*, 1982, 154:513-516.

"Mick 200-TP Applicator Package", Mick Radio-Nuclear Instruments, Inc., advertisement.

"Multiplanar Biopsy Transverse Scan", Bruel & Kjaer Medical Systems, Inc., advertisement.

"Seeding Device—Proscan Urologic Ultrasound Imaging System", Teknar, advertisement.

Sonopsy Ultrasound Guided Breast Biopsy, NeoVision, advertisement.

"Transrectal Biopsy of the Prostate Gland", Bruel & Kjaer Medical Systems, Inc., advertisement.

\* cited by examiner

UTERINE ARTERY OCCLUSION DEVICE WITH CERVICAL RECEPTACLE

FIELD OF THE INVENTION

The invention relates generally to the field of treating uterine disorders of female patients by occluding the patient's uterine arteries.

BACKGROUND OF THE INVENTION

Hysterectomy (surgical removal of the uterus) is performed on approximately 600,000 women annually in the United States. Hysterectomy is often the therapeutic choice for the treatment of uterine cancer, adenomyosis, menorrhagia, prolapse, dysfunctional uterine bleeding, and muscular tumors of the uterus, known as leimyoma or uterine fibroids.

However, a hysterectomy is a major surgical intrusion into a patient's body having attendant risks and many undesirable characteristics. Thus, any method which can provide the therapeutic result of a hysterectomy without removing the uterus would be a significant improvement in this field. Newer treatment methods have been developed for some uterine disorders to avoid removal of the patient's uterus.

For example, in 1995, it was demonstrated that uterine fibroids could be treated without hysterectomy using a non-surgical therapy, specifically comprising bilateral intraluminal occlusion of the uterine arteries (Ravina et al., "Arterial Embolization to Treat Uterine Myomata", Lancet Sep. 9, 1995; Vol. 346; pp. 671-672, incorporated in its entirety herein). This technique is commonly known as "uterine artery embolization". In this technique, uterine arteries are accessed by a delivery catheter via a transvascular route from a common femoral artery into the left and right uterine arteries and an embolization agent such as platinum coils or the like are deposition at a desired location within the uterine arteries. Thrombus quickly forms within the mass of platinum coils at the deployment site to occlude the artery.

The uterus has a dual (or redundant) blood supply, the primary blood supply being from the bilateral uterine arteries, and the secondary blood supply from the bilateral ovarian arteries. Consequently, when both uterine arteries are occluded, i.e. bilateral vessel occlusion, the uterus and the fibroids contained within the uterus are both deprived of their blood supply. However, as demonstrated by Ravina et al., the ischemic effect on the patient's fibroid is greater than the effect on the uterine tissue. In most instances, the uterine artery occlusion causes the fibroid to wither and cease to cause clinical symptoms.

However, many physicians do not possess the training or equipment necessary to perform catheter-based uterine artery embolization under radiologic direction. Accordingly, there are relatively few uterine artery embolizations performed each year in comparison to the number of hysterectomies that have been performed each year for uterine fibroids which are symptomatic.

What is needed, therefore, are simple procedures and the instruments for such procedures for occluding a female patient's uterine arteries without the undesirable features of a hysterectomy that can be used by physicians who do not have the training or equipment for intravascular uterine artery occlusion.

SUMMARY OF THE INVENTION

The invention is directed to a device for occluding a patient's uterine arteries in the treatment of uterine disorders. Specifically, the device embodying features of the invention includes a receptacle which has an interior configured to receive at least part of a female patient's uterine cervix and at least one leading edge of the receptacle which is configured to engage a female patient's vaginal fornix. The receptacle is configured to hold the patient's uterine cervix while the leading edge or edges of the receptacle press against the patient's vaginal fornix to occlude the underlying or adjacent uterine arteries. Preferably, a vacuum source is interconnected to the interior of the cervical receptacle so that upon the application of a vacuum to the interior of the receptacle, the patient's cervix is held within the interior of receptacle. Alternatively, mechanical members may be employed to hold at least part of the patient's cervix within the receptacle.

In one embodiment the leading edge of the cervical receptacle is distally extendible so that it can be pressed against the patient's vaginal fornix to occlude underlying uterine arteries, while the patient's uterine cervix is held within the interior of the receptacle by vacuum or otherwise. The leading edge may have an expandable or inwardly extendible inner portion which has an inwardly extending pressure applying surface so that both an upward and inward thrust may be provided to press against the patient's vaginal fornix to occlude the uterine arteries.

The pressure applying portions of the leading edge of the cervical receptacle are provided with one or more blood flow sensors to detect the location of the uterine arteries when the leading edge of the receptacle is pressed against the patient's vaginal fornix. Once the arteries have been located by the blood flow sensors, the pressure applying surfaces of the leading edge or edges of the cervical receptacle may be further thrust against the vaginal fornix to occlude the underlying uterine arteries. The blood flow sensors on the leading edge may also be used to follow or monitor the uterine artery occlusion by detecting when blood flow terminates and when blood flow is re-established.

When the uterine arteries are located, vacuum can be applied to the interior of the cervical receptacle to pull and hold the uterine cervix and adjacent vaginal fornix tissue into the receptacle interior and hold the cervical and fornix tissue so that the leading edge or edges of the receptacle press against the vaginal fornix wall and occlude the underlying or adjacent uterine arteries.

The uterine artery occlusion effected by the pressure from the leading edge of the receptacle is temporary, and may be partial or complete. Generally, the uterine artery occlusion is less than 48 hours, preferably less than 24 hours for most uterine disorders. Typically about one to about 8 hours is adequate for the treatment of uterine fibroids. Other disorders may require longer or shorter uterine artery occlusion times.

While it is preferred to hold at least part of the patient's uterine cervix within the interior of the cervical receptacle, the cervix receptacle may be provided with a suitable cervical grabbing device or implement or element within the receptacle, such as a tenaculum, to hold the cervix within the interior.

The blood flow sensors on the leading edges of the cervical receptacle for locating a blood vessel may sense sound, pulsation, blood flow or other indicator related to a blood vessel. Thus, a sensor for locating a blood vessel may be a blood flow sensor, a sound sensor, a pressure sensor, a strain sensor, a stress sensor, a chemical sensor, an electromagnetic radiation sensor, or other sensor, and may be a combination of such sensors. A sound sensor may be an ultrasound sensor, including a Doppler ultrasound sensor. The sensor for locating a blood vessel, including a sensor for measuring blood flow, is preferably disposed in or on a pressure-applying surfaces of the leading edges of the cervical receptacle, and are preferably mounted to the face of the tissue-contacting surfaces of the leading edges. The blood flow sensor is preferably oriented perpendicularly to the tissue contacting surfaces of the leading edges, although other orientations may be employed.

Ultrasound energy useful for sensing a location of a blood vessel or of blood flow in a blood vessel may have a frequency of less than about 20 MegaHertz (MHz), such as between about 5 MHz and about 19 MHz, preferably between about 6 MHz and about 10 MHz, more preferably a frequency of about 8 MHz. Electromagnetic energy useful for sensing a location of a blood vessel or of blood flow in a blood vessel may have a wavelength of between about 500 nanometers (nm) and about 2000 nm, preferably between about 700 nm and about 1000 nm.

In an alternate embodiment, the cervical receptacle is configured with the interior chamber thereof large enough so that upon the application of a vacuum to the interior chamber, the patient's cervix is pulled into the interior chamber sufficiently to cause the leading edges to apply pressure through the patient's vaginal fornix to occlude the uterine arteries adjacent to or underlying the vaginal fornix.

The non-invasive devices and systems embodying features of the invention allow for the non-surgical location and occlusion of uterine arteries without the puncture of bodily tissue, and without the need for radiographic equipment or for skill in the use of radiographic techniques. The devices and methods are simpler and more readily used and removed than other methods and devices, and provide improved treatments for uterine disorders that might otherwise require invasive and irreversible treatments such as removal of a hysterectomy.

These and other advantages of the invention will become more apparent from the following detailed description of the invention when taken in conjunction with the accompanying exemplary drawings.

DETAILED DESCRIPTION OF THE INVENTION

Figure 1:
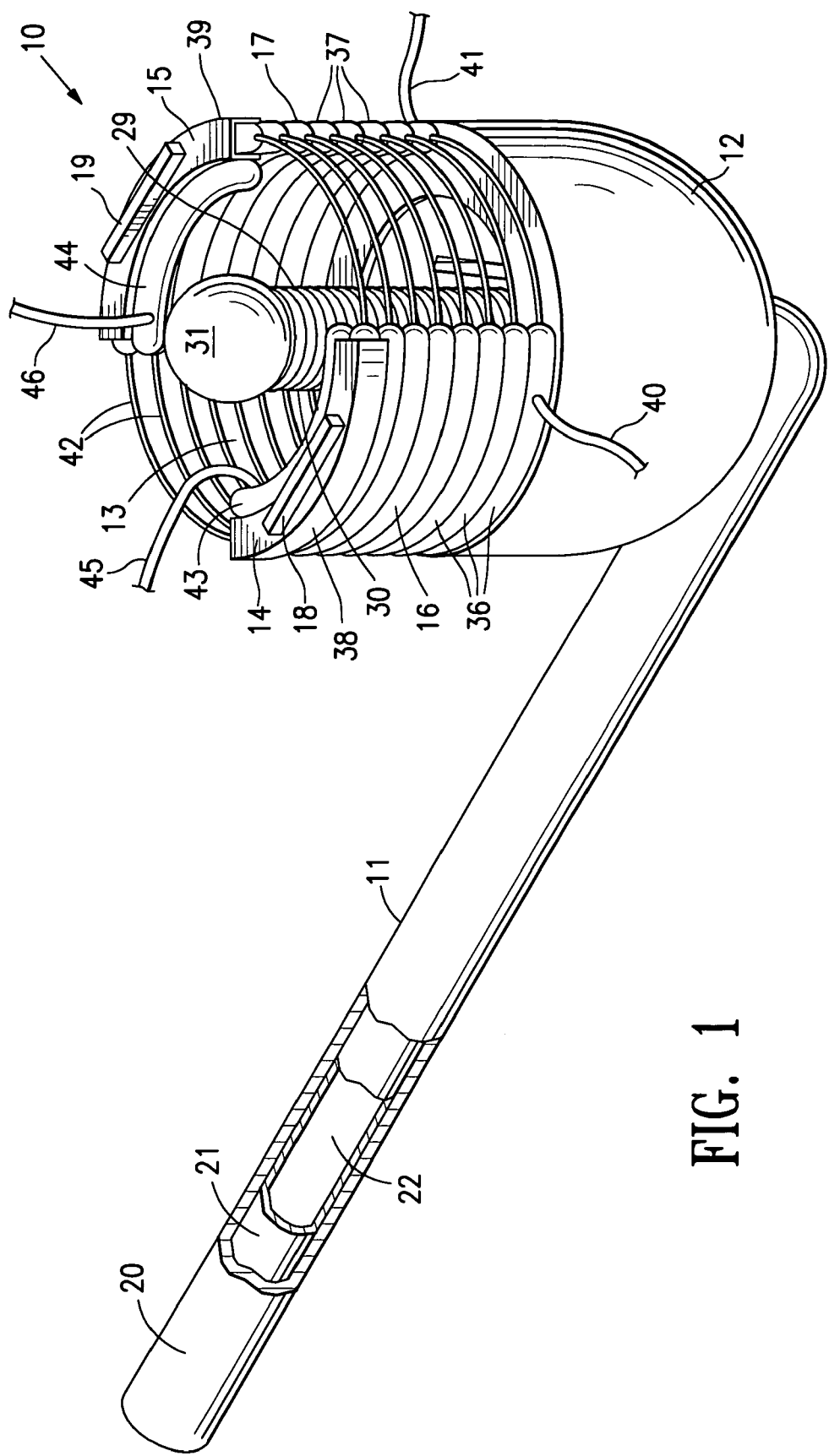
FIG. 1 is a partial perspective view of a uterine artery occluding device embodying features of the invention which has a cervical receptacle and an elongated shaft.
Figure 2:
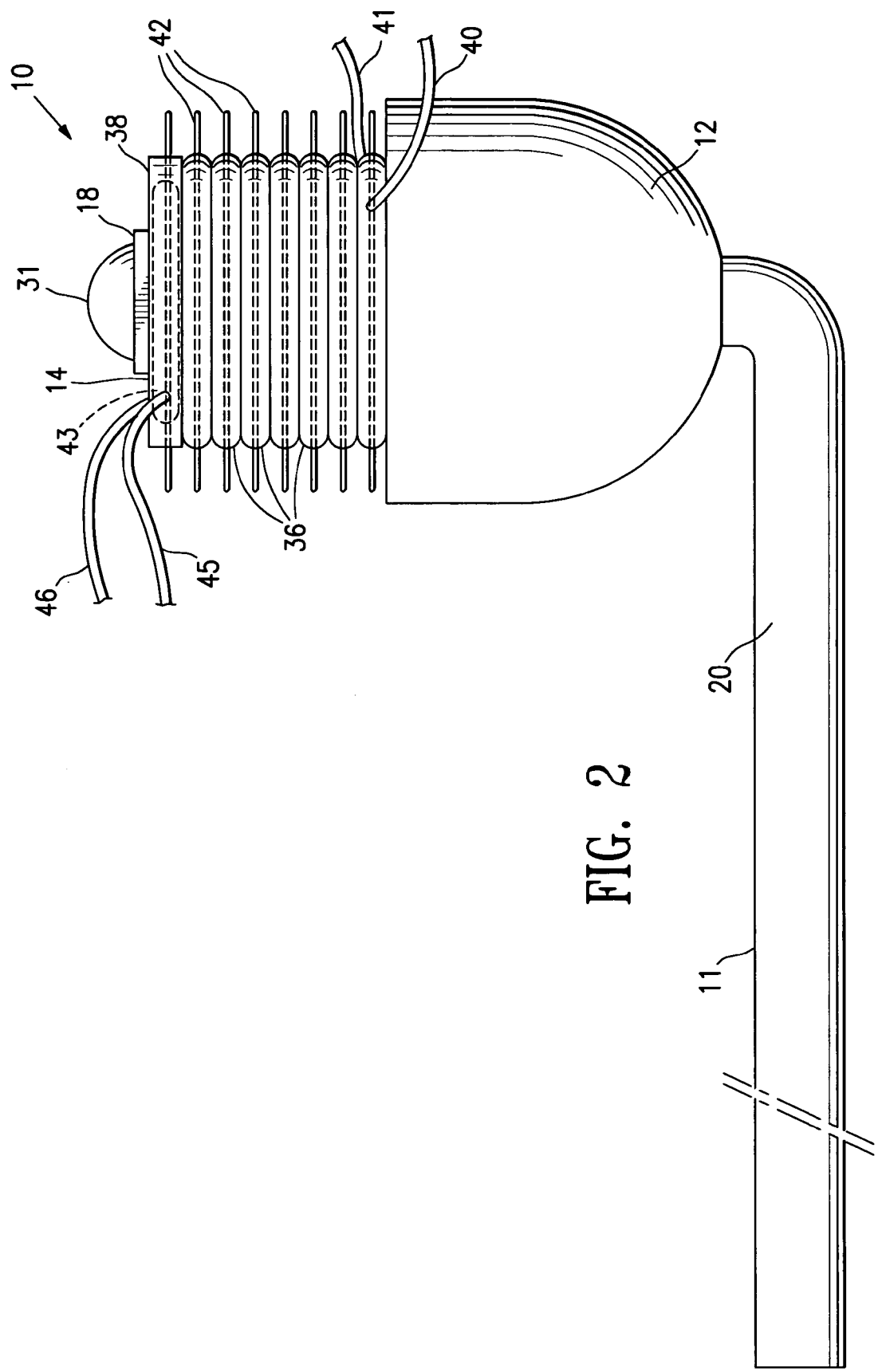
FIG. 2 is an elevational view of the uterine artery occlusion device shown in FIG. 1.
Figure 3:
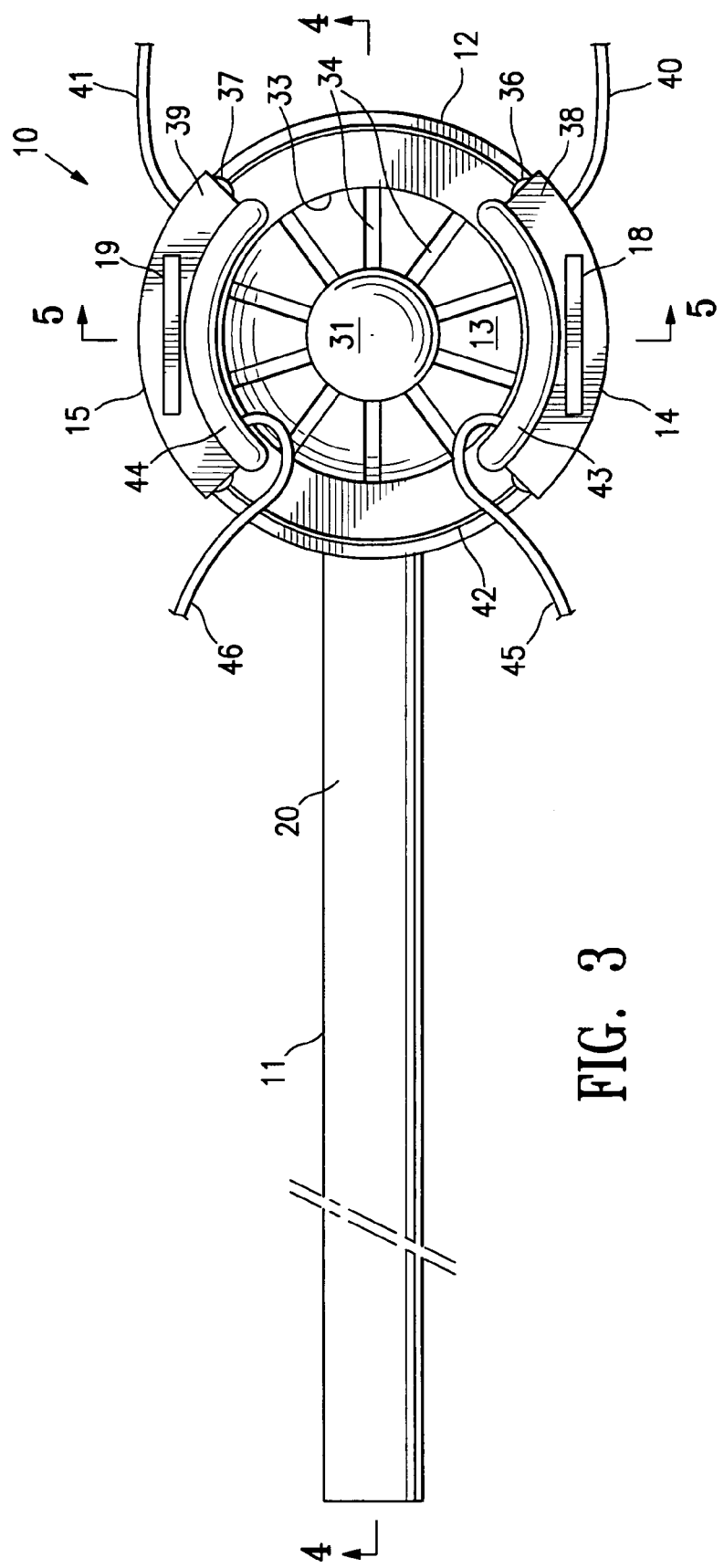
FIG. 3 is a plan view of the occlusion device shown in FIG. 1.
Figure 4:
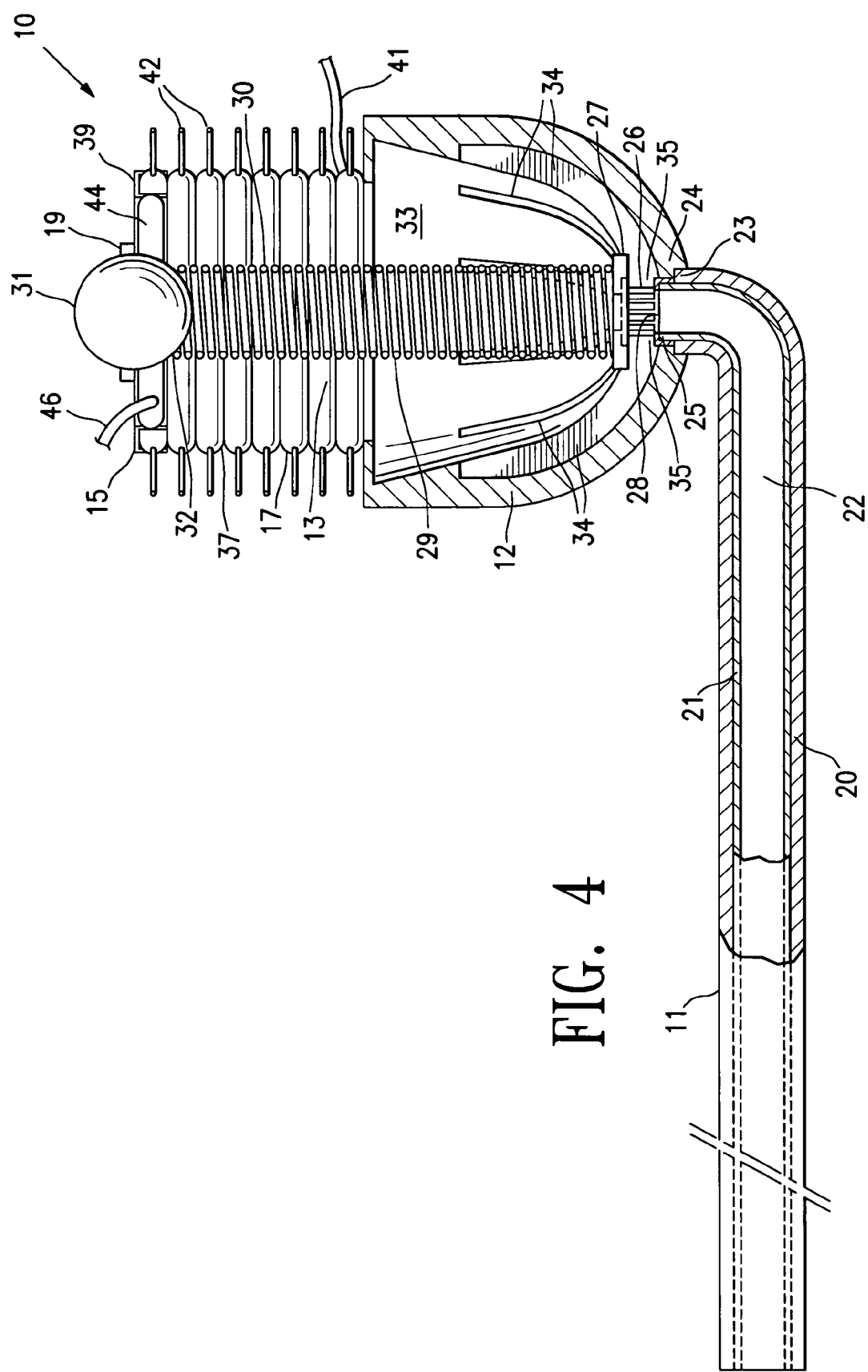
FIG. 4 is a longitudinal cross-sectional view of the occlusion device shown in FIG. 1, taken along the lines 4-4 shown in FIG. 3.
Figure 5:
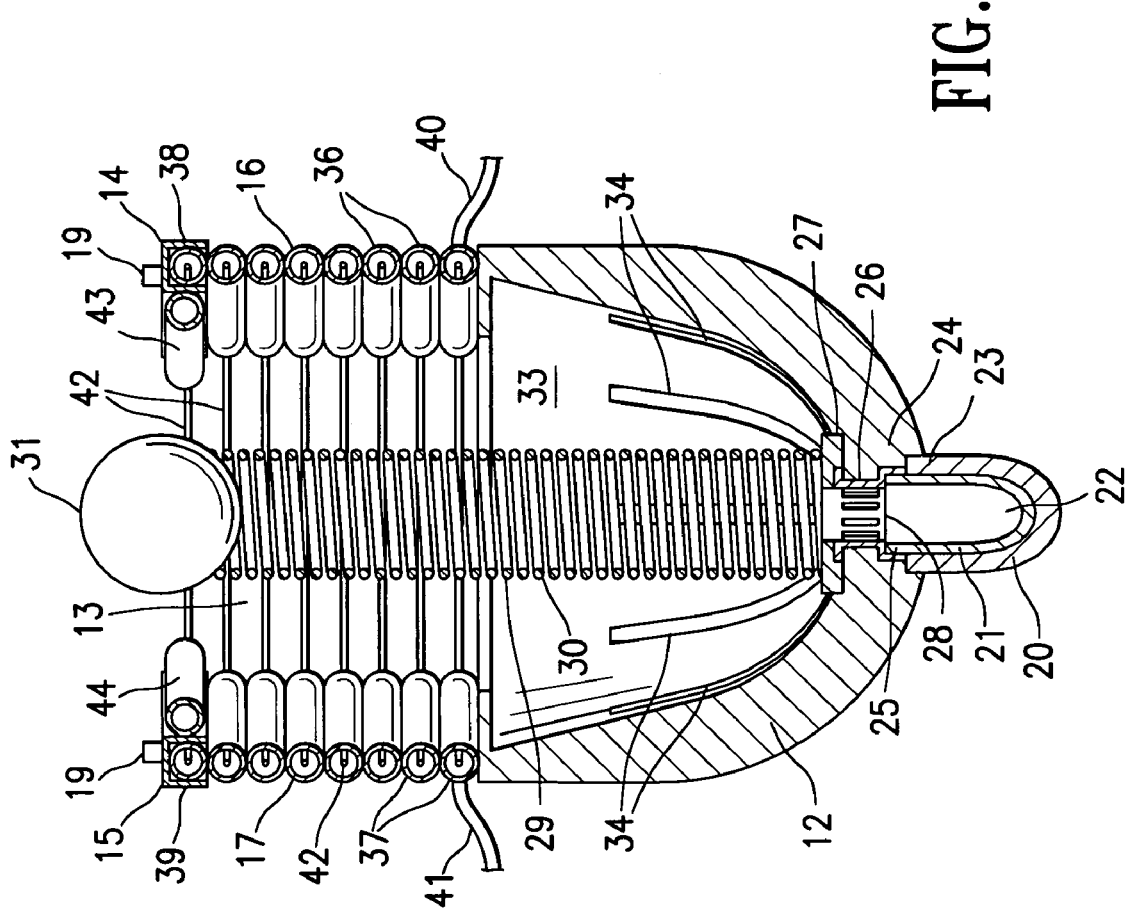
FIG. 5 is a transverse cross-sectional view of the occlusion device shown in FIG. 1 taken along the lines 5-5 shown in FIG. 3.

FIGS. 1-5 show an intravaginal uterine artery occluding device 10 embodying features of the invention. The device 10 includes an elongated shaft or handle 11 and a cervical receptacle 12 on the distal end of the shaft which has an interior chamber 13 configured to receive at least part of the patient's uterine cervix and which has leading edges 14 and 15 for applying pressure to the patient's vaginal fornix adjacent the uterine cervix to occlude underlying or adjacent uterine arteries. Distally extendable curtains 16 and 17 are secured at their proximal ends to the open distal end of receptacle 12 and leading edges 14 and 15 are secured to the distal ends of curtains 16 and 17 respectively. Blood flow sensors 18 and 19 are provided on the leading edges 14 and 15 to aid in the location of the patient's uterine arteries.

The elongated shaft 11 is formed of outer and inner tubular members 20 and 21 respectively and has an inner lumen 22 extending within the inner tubular member 21. The distal end 23 of outer tubular member 20 is secured to the base 24 of the cervical receptacle 12 and the distal end 25 of inner tubular member 21 extends through the base 24. Grating 26 supports the base plate 27 away from the opening 28 in the distal end 25 of inner tubular member 21 to provide fluid communication between the inner lumen 22 and the interior chamber 13 of receptacle 12. Cervical sound or post 29 is secured to (e.g. by soldering or brazing) and supported by base plate 27 centrally within the interior chamber 13 of the receptacle 12. The cervical post 29 is formed of a helical coil 30 which has a spherical plug 31 secured to the distal end 32 thereof by solder, brazing and the like (not shown) to present a non-traumatic tip for insertion into the patient's cervical canal.

The inner bowl 33 of the receptacle 12, which defines at least in part the interior chamber 13, has a plurality of vertically oriented grooves 34 disposed around the inner bowl. The proximal ends 35 of the grooves 34 are adjacent to the openings in the grating 26 and are configured to disperse the vacuum conditions provided by the inner lumen 22 of the shaft 11 about the interior chamber 13 defined by the inner bowl 33. The distal ends of the grooves 34 extend toward the upper open end of the receptacle 12 a sufficient distance to ensure that the vacuum applied to the cervical tissue in the receptacle will hold the received portion of the cervix within the receptacle during the procedure of occluding the uterine arteries.

The distally extending curtains 16 and 17 of the occluding device 10 shown in FIGS. 1-5 are arc-shaped and are formed by a plurality of arcuate inflatable members 36 and 37 respectively. Generally, u-shaped support members 38 and 39 are provided on the distal ends of curtains 16 and 17 to form the leading edges 14 and 15 which apply the pressure required to occlude a patient's uterine arteries. The blood flow sensors 18 and 19 are secured to the leading edges 14 and 15 to locate the patient's uterine arteries and monitor blood flow therethrough. The distally extending curtains 16 and 17 are formed of suitable relatively non-compliant polymeric material such as polyethylene terepthalate, polyesters such a Hytrel, Nylon 6, poly(vinyl chloride), polyurethane and the like. The inflatable members 36 and 37 are provided with inflatable fluid through inflation tubes 40 and 41 respectively which are in fluid communication with the interior of the inflatable members 36 and 37 adjacent to the open distal end of the receptacle 12. The interiors of the individual inflatable members of the curtains 16 and 17 are secured together and preferably in fluid communication so that all of the interiors of the inflatable members of a particular curtain receive inflation fluid from a single inflation tube. Circular support members 42 extend longitudinally through the inflatable members 36 and 37 which are sealed at their respective ends about the support members 42. Support members 42 maintain the relative positions of the individual curtains 16 and 17 during storage, deployment and use even though the curtains may be independently inflated. Typically, the support members are metallic wire members about 0.015 to about 0.3 inch in diameter and are formed of NiTi alloy or stainless steel.

The upper or distal portion of the extending curtains 16 and 17, for example the depending portion of support members 38 and 39 are preferably provided with an inwardly expansive inflatable members 43 and 44 which are formed of compliant polymeric material such as polyurethane, silicone, polyolefin elastomers and C-Flex®. The inwardly expansive inflatable members 43 and 44 are inflated through inflation tubes 45 and 46 respectively.

Figure 6:
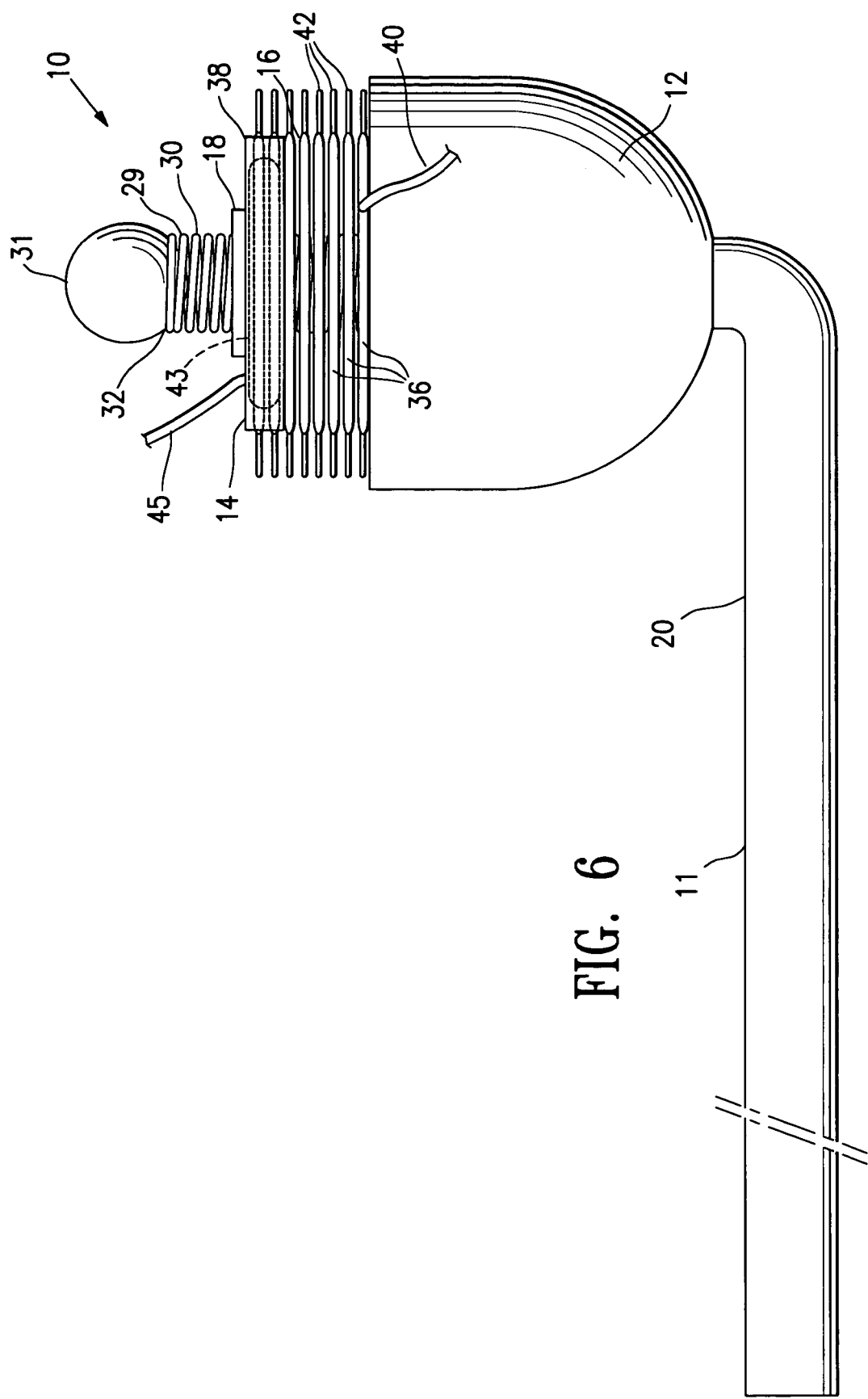
FIG. 6 is an elevational view of the occlusion device as shown in FIG. 2 with the extendable curtains in un-inflated conditions.

FIGS. 1-5 illustrate the extendable curtains 16 and 17 in the inflated condition, whereas FIG. 6 illustrates the expandable curtains in the uninflated condition.

Figure 7:
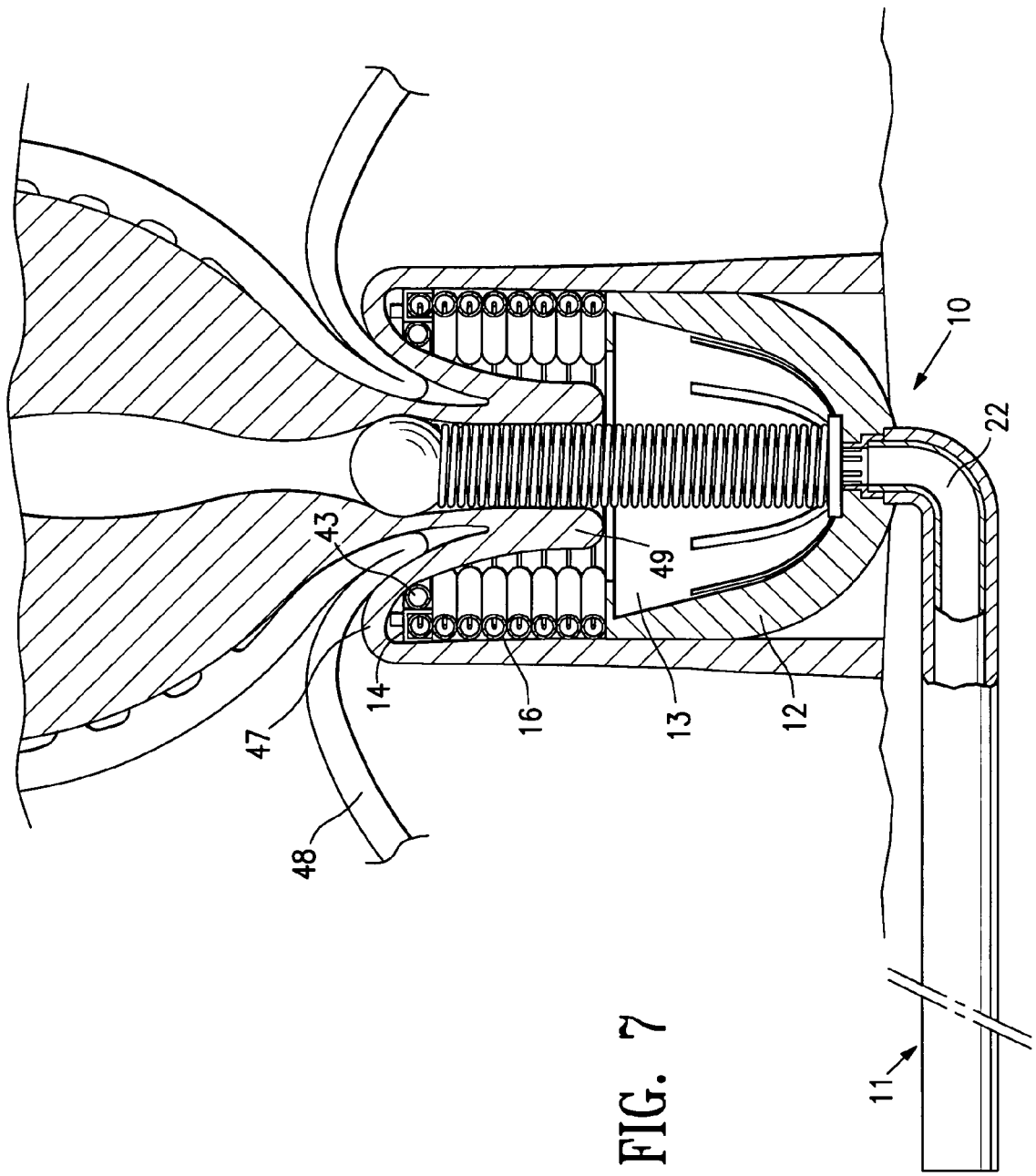
FIG. 7 is a partial schematic diagram of a reproductive system of a human female with an extendable curtain of the occluding device shown in FIG. 1 pressed against the patient's vaginal fornix to occlude the underlying uterine artery.

FIG. 7 illustrates the device positioned within the patient with the leading edge 14 on the distal end of the extendable curtain 16 in the expanded condition pressing against the vaginal fornix 47 and at least partially occluding the patient's left uterine artery 48. The side expansion balloon 43 expands inwardly to further press against the vaginal fornix 47 to ensure the occlusion of the patient's left uterine artery 48. The patient's uterine cervix 49 is held within the interior chamber 13 of receptacle 12 by the application of a vacuum through the inner lumen 22 of the shaft 11 throughout the treatment.

The shaft 11 and the elbow at the distal end of shaft 11 leading to the receptacle 12 is flexible enough so that the receptacle can rotate with respect to the end of the shaft 11 to facilitate the introduction and advancement of the device 10 within the patient's vaginal canal. A delivery sheath (not shown) may be employed to facilitate such delivery. The receptacle 12 may be sufficiently flexible to be collapsed prior to insertion into the patient's vaginal canal.

Figure 8:
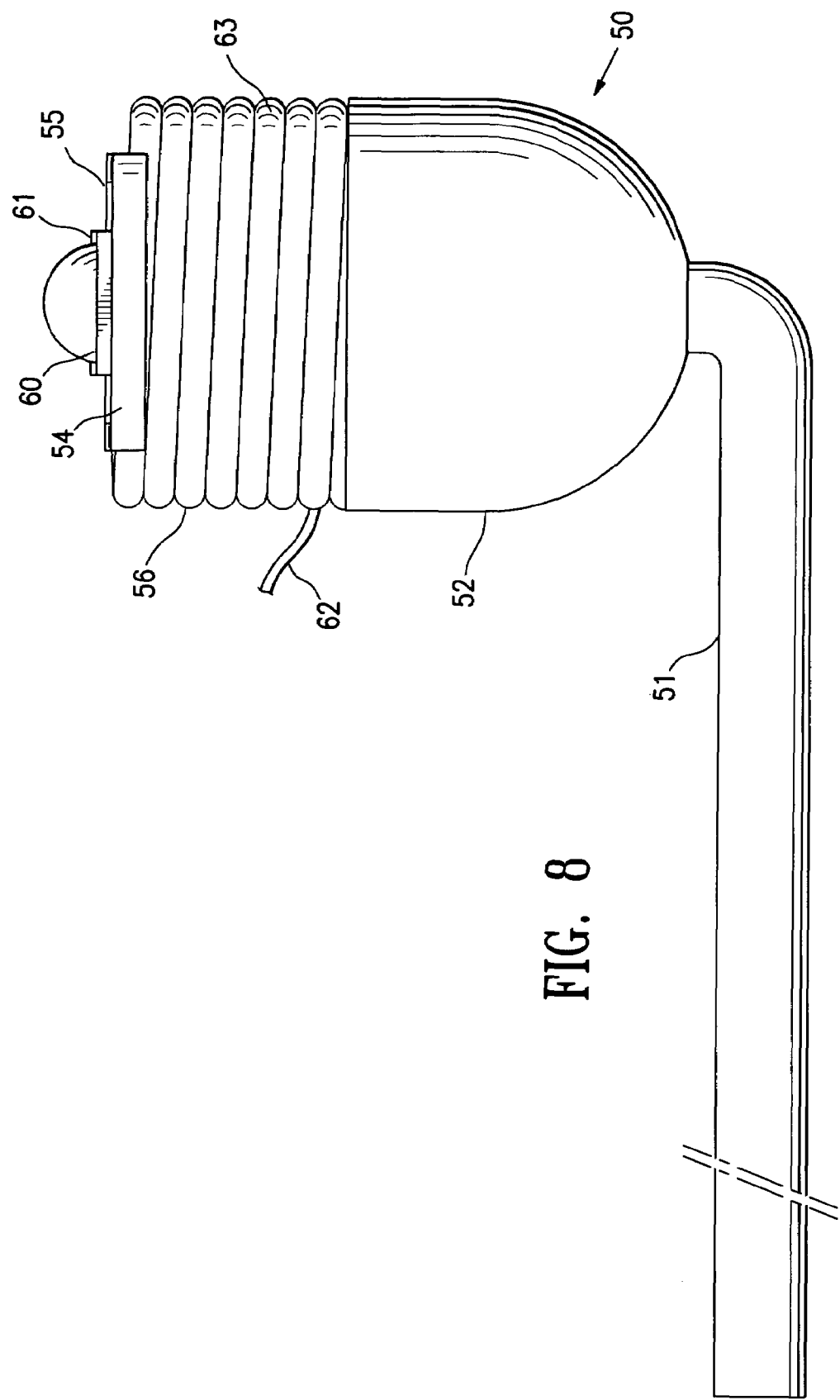
FIG. 8 is an elevational view of an alternative uterine artery occlusion device embodying features of the invention with a cylindrically shaped extendable curtain.
Figure 9:
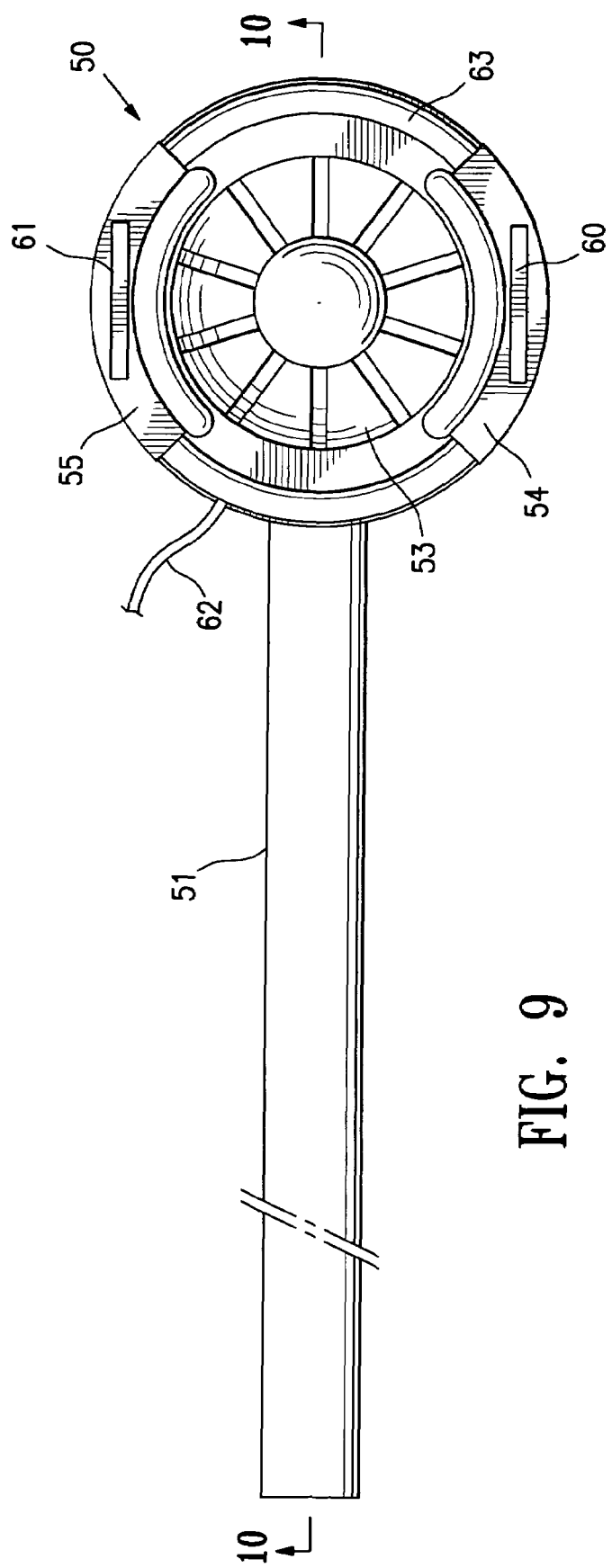
FIG. 9 is a plan view of the uterine artery occlusion device shown in FIG. 8.
Figure 10:
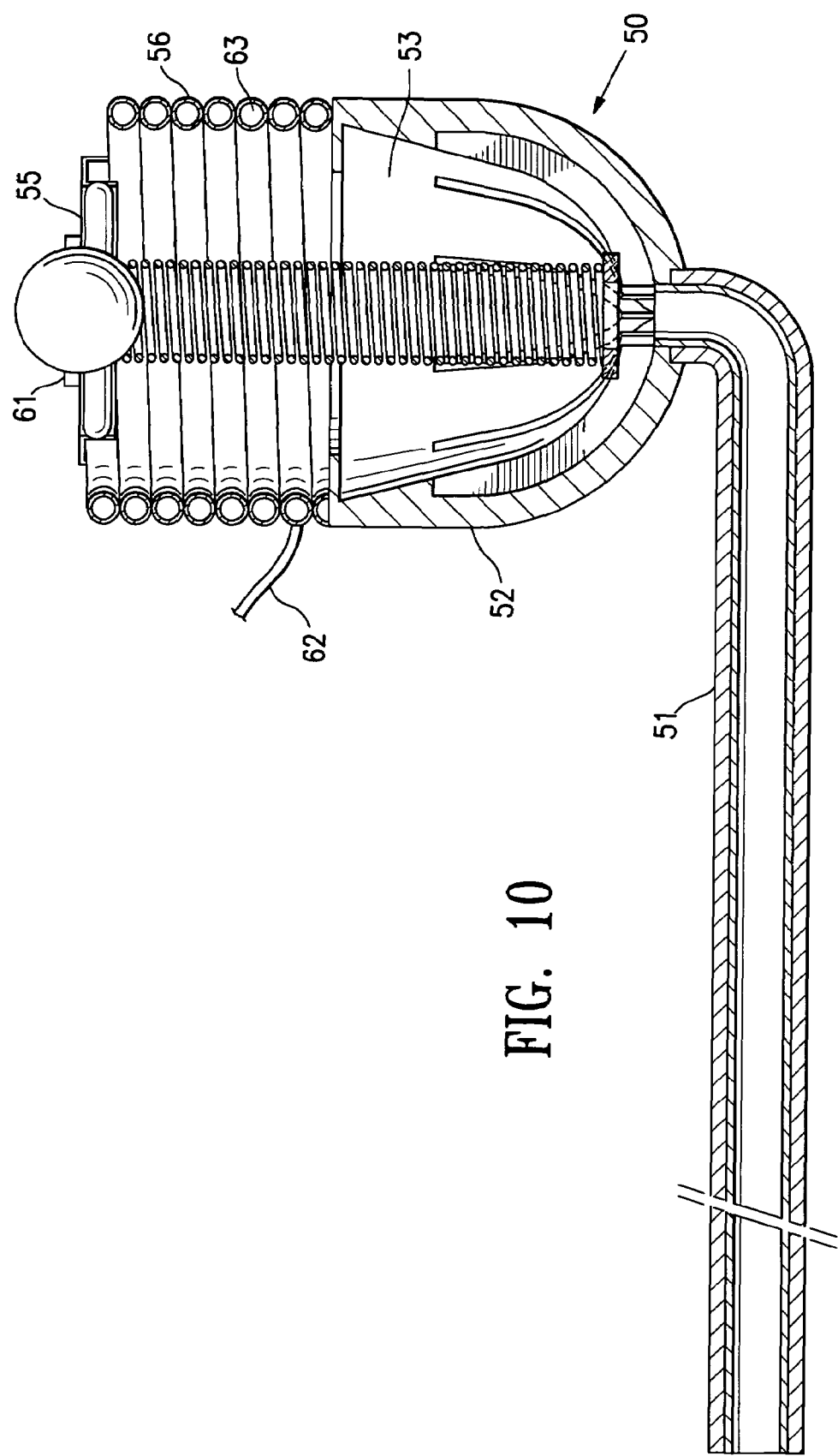
FIG. 10 is a longitudinal cross-sectional view of the device shown in FIG. 9, taken along the lines 10-10.

FIGS. 8-10 illustrate another occlusion device 50 which embodies features of the invention. This embodiment is similar in most respects as the embodiment shown in FIGS. 1-4. The device 50 shown has an elongated shaft 51, a cervical receptacle 52 with an interior chamber 53 and with leading edges 54 and 55. A cylindrical, distally extending curtain 56 is provided with the proximal end of the curtain secured to the open distal end of the receptacle 52. The leading edges 54 and 55 are secured to opposite sides of the distally extending cylindrical curtain 56 and are provided with blood flow sensors 60 and 61 respectively to locate the patient's uterine arteries and preferably also monitor the flow of blood flow through these arteries. The distally extending curtain 56 is preferably provided with an inflation tube 62 so that the curtain can be distally extended when inflation fluid is directed to the interior of the helically shaped inflatable member 63 of the curtain 56. The device 50 is otherwise the same as the device as previously described for FIGS. 1-6.

Figure 11:
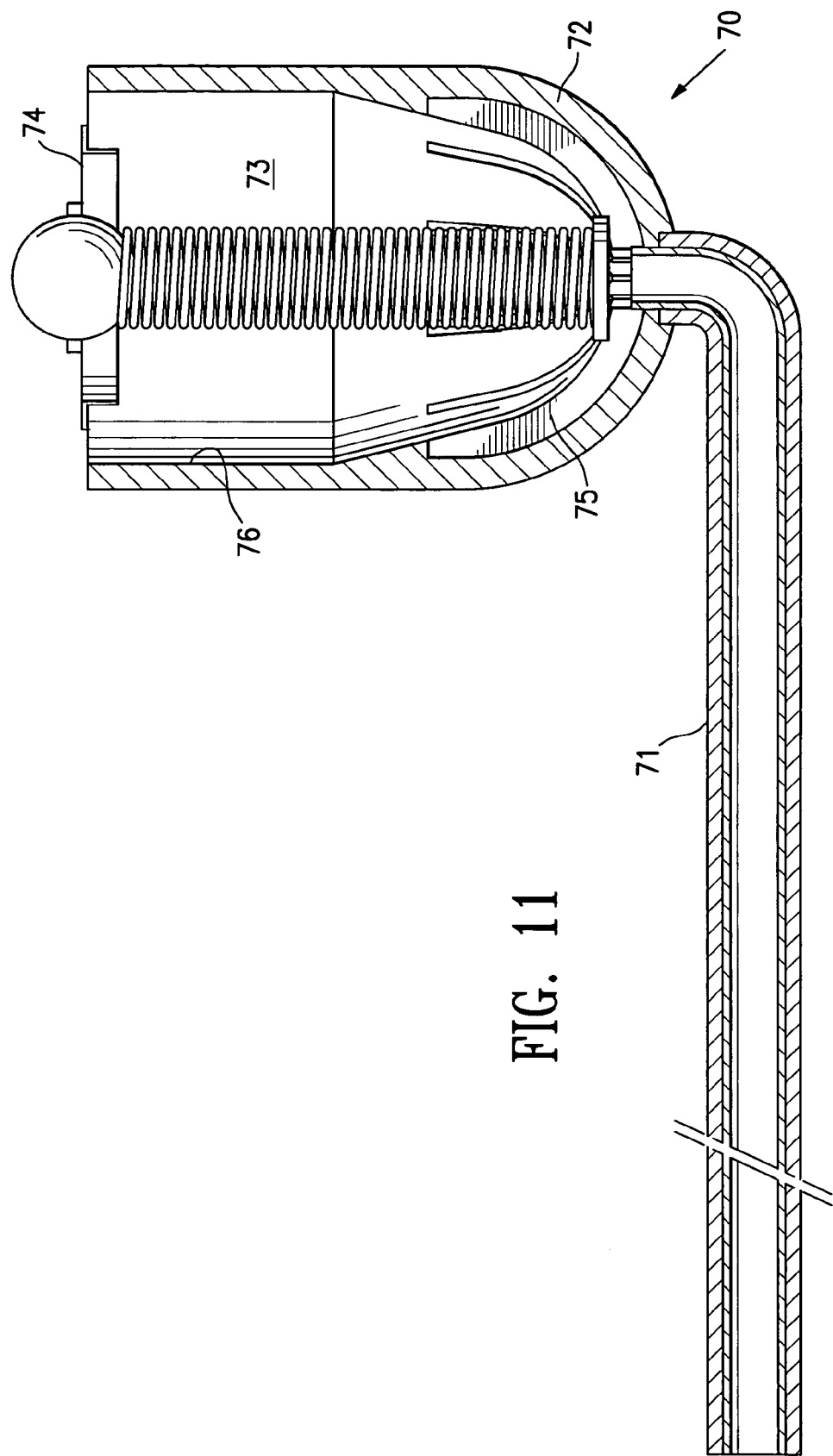
FIG. 11 is an elevational view partially in section of an alternative cervical receptacle without one or more distally extendable leading edges.

FIG. 11 illustrates an alternative uterine artery occlusion device 70 which has an elongated shaft 71, cervical receptacle 72 with interior chamber 73 and leading pressure applying edge 74 similar to the prior embodiments. However, occlusion device 70 does not have one or more distally extendable curtains as do the previously described embodiments. Grooves 75 are provided on the inner surface 76 of receptacle 72 which disperse the vacuum as in the prior embodiments. In this embodiment the receptacle 72 is configured large enough to receive the patient's uterine cervix and part of the patient's vaginal fornix when vacuum is applied to the interior chamber 75. As vacuum is applied to pull in the cervical and vaginal tissue, the leading edge 74 presses against the wall of the patient's vaginal fornix to occlude the underlying or adjacent uterine arteries.

Figure 12:
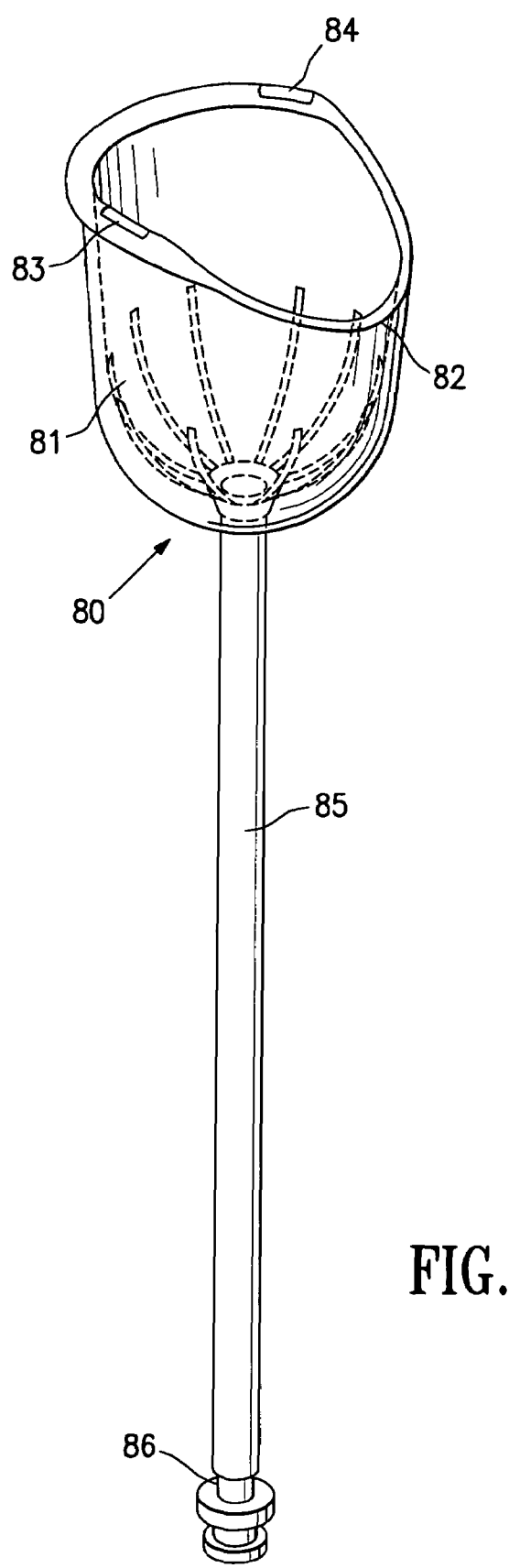
FIG. 12 is a perspective view of an alternative cervical receptacle with a lowered anterior lip.

Another alternative embodiment is illustrated in FIG. 12 where the occlusion device 80 has a cervix receiving bowl 81 which has a lowered anterior lip 82 to facilitate positioning the bowl about the patient's uterine cervix prior to the application of pressure to the patient's uterine arteries for the occlusion thereof. Blood flow sensors 83 and 84 are provided on the upper surface of the bowl 81 as in the other occlusion devices described herein. The shaft 85 has a leur connector 86 (or other suitable connector) configured to be connected to a vacuum source. The interior of the bowl 81 is the same as in the previously described devices. The operation of the device is essentially the same, except that the bowl 81 is easier for the physician to position about the patient's uterine cervix.

Figure 13:
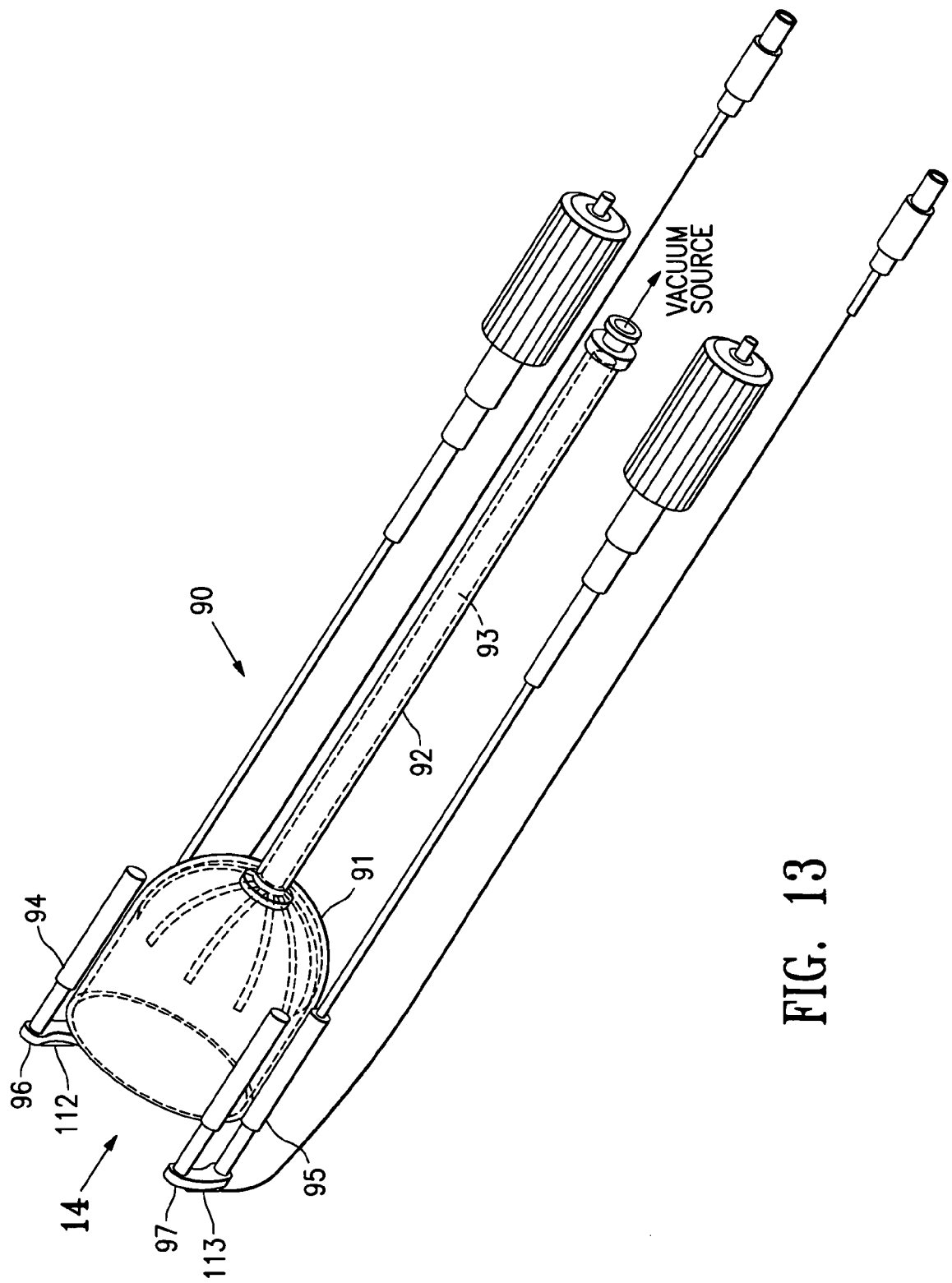
FIG. 13 is a perspective view of an alternative cervical receptacle wherein hydraulically operated pressure applicators are secured to the receptacle bowl.
Figure 14:
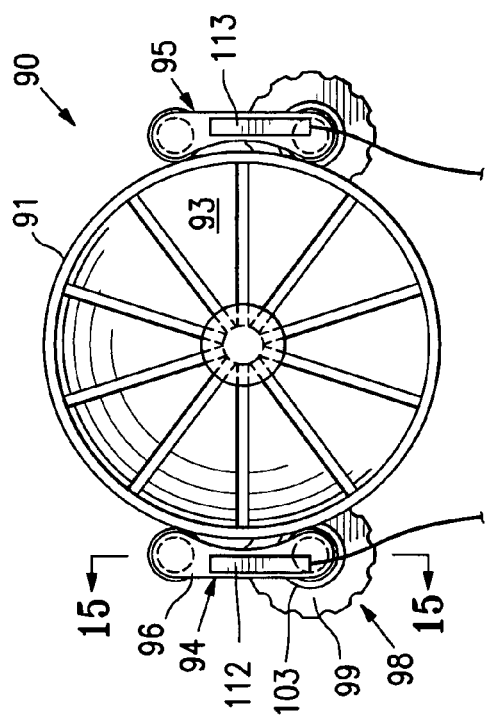
FIG. 14 is an end view of the cervical receptacle shown in FIG. 13.
Figure 15:
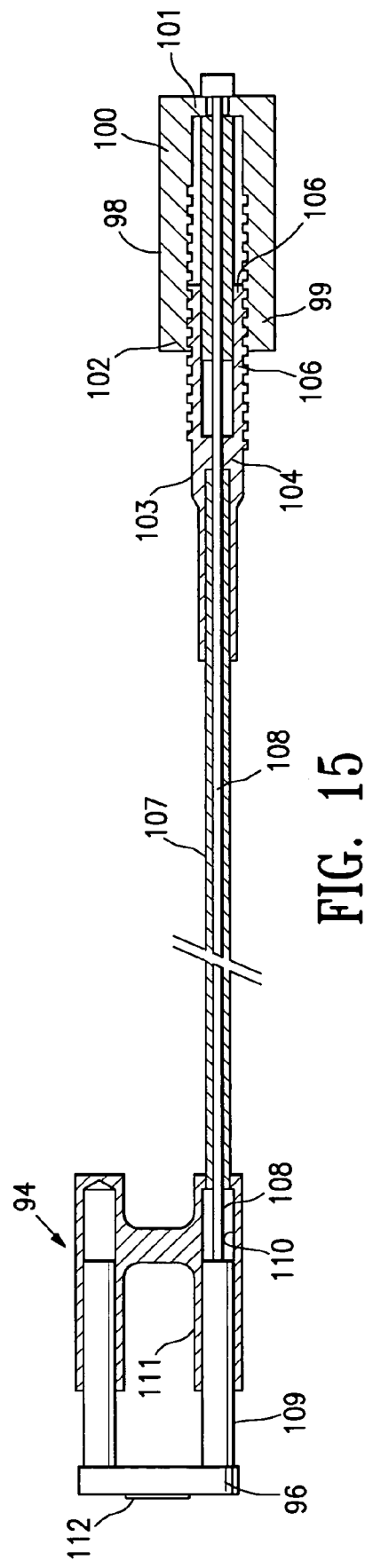
FIG. 15 is a longitudinal cross-sectional view taken along the lines 15-15 shown in FIG. 14.

FIGS. 13, 14 and 15 illustrate an alternative embodiment where the occlusion device 90 has a cervix-receiving bowl 91 secured to the distal end of an elongated shaft 92 which has an inner lumen 93 in fluid communication with the interior of the bowl 91 as in the other embodiments. Mechanically operated, pressure applying heads 94 and 95 are provided on each side of the bowl 91 which have extendable occlusion bars 96 and 97 configured to occlude a patient's uterine arteries. Details of the mechanical operation of the pressure bars 96 and 97 are best shown in the longitudinal cross-sectional view shown in FIG. 15.

As shown in FIG. 15, the operable handle 98 includes a housing 99 having a first cylindrical member 100 with one closed end 101 and one open end 102 and a second cylindrical member 103 with one closed end 104 and one open end 105. The open ends of the first and second cylindrical members interfit, with the open end 102 of the first cylindrical member 100 having a threaded interior and the open end 105 of the second cylindrical member 103 having a threaded exterior. Drive shaft 106 is secured to the closed end 101 the first cylindrical member 100 and is rotatable and longitudinally slidable through the closed end 104 of the second cylindrical member 103 so that rotation of one of the cylindrical members with respect to the other adjusts the distance between the closed ends of the first and second cylindrical members 100 and 103. The drive shaft 106 extends through outer tubular member 107 which is secured by its distal end to the head 94 and by its proximal end to the closed end 104 of the cylindrical member 103. The tubular member 107 is preferably a relatively flexible tube. The distal end 108 of the drive shaft 106 engages the end of leg 109 which is slidably disposed within the recess or bore 110 in arm 111 of pressure applying head 94. Upon contraction of the distance between the closed ends of the cylindrical members 100 and 103, the drive shaft 106 is driven through the outer tubular member 107 and the distal end 108 is urged against the leg 109 which depends from the under side of occluding bar 96, and in turn drives the occlusion bar 96 attached to the leg 109 distally away from the cervical receptacle 91. This structure allows the operator to fix the bowl 91 about the patient's uterine cervix and then use the mechanically operated occlusion bars 96 and 97 to occlude the patient's uterine arteries. The occlusion bars 96 and 97 are provided with blood flow sensors 112 and 113 on the pressure applying surfaces thereof. The pressure applying heads 94 and 95 may also be hydraulically driven. The cervical receptacle 91 may be provided with a lowered lip 82 as shown in FIG. 12. The pressure applying head 95 is essentially the mirror image of pressure head 94 and is operated in the same manner.

The embodiment shown in FIGS. 13-15 is used in a similar fashion as the prior embodiments. The cervical receptacle 91 and attached shaft 92 are inserted into the patient's vaginal canal and advanced therein until the patient's uterine cervix is disposed at least in part within the interior of the receptacle. A vacuum is applied to the interior of the receptacle 91 by pulling a vacuum in inner lumen 93 filling the receptacle with at least the lower portion of the patient's uterine cervix and holding the position thereof. The handle of the first cylindrical member 100 is manually rotated to drive the occlusion bar 96 against the patient's vaginal fornix. The blood flow sensor 112 on the occlusion bar 96 is utilized to locate the patient's uterine artery and monitor the blood flow therethrough. The other occlusion bar may be advanced against the patient's vaginal fornix in the same manner. The device is left in place until the uterine arteries have been occluded for sufficient time to provide the desired therapeutic effects, at which time the vacuum may be released and the device removed from the patient. A strap (not shown) may be provided about the pressure applying heads 95 and 96 to apply a side force against the heads to further apply and hold pressure against the fornix and cervix of the patient to ensure uterine artery occlusion.

A preferred blood flow sensor is a Doppler ultrasound sensor operating at ultrasound frequencies less than about 20 MHz, such as between about 5 MHz and about 19 MHz, preferably between about 6 MHz and about 10 MHz and typically about 8 Hz, is suitable for detecting blood flow in an artery with apparatus embodying features of the invention. Suitable commercially available blood flow sensors include ultrasonic Doppler sensors such as the MedaSonics® CardioBeat® Blood Flow Doppler with Integrated Speaker (Cooper Surgical, Inc., Trumbull Conn. 06611)), the Koven model ES 100X MiniDop VRP-8 probe (St. Louis, Mo.) and the DWUNeuro Scan Medical Systems' Multi-Dop B+ system (Sterling, Va.).

Sufficient pressure or force applied to the tissue of the vaginal fornix to compress and to at least partially occlude the underlying or adjacent uterine artery. For effective therapeutic treatments, the uterine arteries should remain occluded for a limited time, usually less than 48 hours, for treating uterine disorders. A suitable limited time may be between about 0.2 hours and about 24 hours, preferably between about 0.5 hour and about 12 hours for most uterine disorders.

The uterine arteries of adult human females are located adjacent the vaginal mucosa at a location within a few centimeters (cm) of the vaginal fornix. Thus, for accessing and occluding a uterine artery, the dimensions of the patient's vaginal opening and canal help to determine suitable sizes for the occlusion devices embodying features of the invention. At least a portion of the occlusion device is configured to be introduced and advanced within the patient's vaginal canal to the patient's uterine cervix. Moreover, the shaft of the device is configured so that the device can be manipulated within the vaginal canal and readily reach the vaginal fornix when operated from outside of a patient's body. For example, the vacuum based occlusion device may be about 4 inches to about 16 inches in length, preferably about 6 inches to about 12 inches in length.

Non-invasive artery occluding devices embodying features of the invention may be made from any suitable material or combination of materials, including biocompatible polymers, such as polycarbonate, polysulfone, polyester and polyacetal, metals such as stainless steel and shape memory alloys such as nickel titanium alloys, plastics, ceramics, and other materials known in the art. The device or system may be designed for single use (disposable) or may be sterilizable and capable of multiple use.

While particular forms of the invention have been illustrated and described, it will be apparent that various modifications can be made to the invention. For example, the invention is described herein primarily with the use of a vacuum to hold the patient's uterine cervix within the receptacle. Other means including mechanical means such a rotating members may be employed to hold the patient's cervix within the interior or the receptacle. Accordingly, the invention is not to be limited to the specific embodiments illustrated and it is to be defined by the appended claims as broadly as the prior art will permit, and in view of the specification if need be. Moreover, those skilled in the art will recognize that features shown in one embodiment may be utilized in other embodiments.

Terms such a "element", "member", "device", "sections", "portion", "section", "means", "steps" and words of similar import when used herein shall not be construed as invoking the provisions of 35 U.S.C. §112(6) unless the following claims expressly use the term "means" followed by a particular function without specific structure or the term "step" followed by a particular function without specific action.

What is claimed is:

1. An intravaginal uterine artery occlusion device, comprising:
   a. an elongated shaft which has a distal end, an inner lumen configured to be interconnected to a vacuum source and extending to the distal end;
   b. cervical receptacle which is secured to the distal end of the elongated shaft, which has an open distal end and an interior configured to receive at least part of a female patient's uterine cervix and which has at least one groove in a wall of the cervical receptacle in fluid communication with the inner lumen of the shaft; and
   c. a wall portion at the open distal end of the cervical receptacle which has an extendable curtain having a proximal end secured to the open distal end of the cervical receptacle and a distal end that is configured to extend distally from the open distal end of the receptacle and that has at least one distal pressure applying surface to facilitate occlusion of the patient's uterine artery.

2. The device of claim 1, wherein the cervical receptacle is configured to be disposed about the patient's uterine cervix when the extendable curtain is distally extended so that the pressure applying surface thereon applies pressure to the patient's vaginal fornix.

3. The device of claim 1, wherein the extended curtain comprises inflatable members.

4. The device of claim 1, wherein the extendable curtain is cylindrically shaped.

5. The device of claim 1 including a pair of opposed extendable curtains, with each curtain having a proximal end secured to the cervical receptacle and a distal end which has a pressure applying surface.

6. The device of claim 4, wherein the extendable curtain comprise inflatable members.

7. The device of claim 1, wherein the distal pressure applying surface has a blood flow sensor to facilitate location of the patient's uterine artery.

8. The device of claim 7, wherein the blood flow sensor is a Doppler ultrasound sensor.

9. The device of claim 8, wherein the Doppler sensor is configured to sense ultrasound energy having a frequency of between about 5 MHz and about 19 MHz.

10. The device of claim 8, wherein the Doppler ultrasound sensor is configured to sense ultrasound energy having a frequency of between about 6 MHz and about 10 MHz.

11. The device of claim 8, wherein the Doppler ultrasound sensor is configured to sense ultrasound energy having a frequency of about 8 MHz.

12. The device of claim 8, wherein at least one blood flow sensor has a sensing direction distally away from the pressure applying surface of the wall portion to facilitate detection of the patient's uterine artery.

13. The device of claim 1, wherein the cervical receptacle has an elongated cervical sound within the interior thereof configured to be guided into a female patient's cervical canal to thereby position the receptacle about the exterior of the patient's cervix.

14. The device of claim 13, wherein the elongated cervical sound is provided with a rounded non-traumatic distal tip.

15. The device of claim 1, wherein the cervical receptacle has at least one groove in an inner surface.

16. The device of claim 14, wherein the at least one groove is parallel to a central axis of the receptacle.

17. The device of claim 1, wherein the interior of the receptacle is configured to receive the patient's cervix and part of the patient's vaginal fornix so that the pressure applying surface applies sufficient pressure to the vaginal fornix to occlude the patient's uterine artery.

18. The device of claim 1, wherein the pressure applying surface is part of an occlusion bar.

19. An intravaginal system for occluding a female patient's uterine artery, comprising:
  a. a cervical receptacle which has
    an open distal end with at least one distally extendable curtain secured thereto having a leading pressure applying edge,
    a closed proximal end,
    an interior chamber configured to receive at least part of a female patient's uterine cervix through the open distal end,
    an opening in the closed proximal end,
    at least one groove in a wall of the cervical receptacle;
  b. at least one blood flow sensor in or on leading pressure applying edge of the extendable curtain to facilitate location of the patient's uterine artery to be occluded; and
  c. an elongated shaft which has a proximal end and a distal end secured to the proximal end of the cervical receptacle, which has an inner lumen interconnected with a vacuum source at one end and in fluid communication with the groove through the opening in the closed proximal end of the receptacle at the other end.

20. The non-invasive blood vessel occlusion device of claim 18, comprising a plurality of sensors.

21. An intravaginal method of treating a female patient's uterine disorder which includes occluding at least one of the female patient's uterine arteries, comprising:
  a. providing a uterine artery occlusion device having a cervical receptacle with an open distal end and a closed distal end, an interior chamber which is configured to receive at least part of the patient's uterine cervix Through the open distal end and which has at least one pressure applying surface which is part of at least one distally extendable curtain, and an elongated shaft having an inner lumen which has a distal end in fluid communication with the interior of the receptacle and a proximal end configured for interconnection with a vacuum source;
  b. inserting the uterine artery occlusion device within the patient's vaginal canal and advancing the device therein until the receptacle is adjacent to the patient's uterine cervix.
  c. positioning the receptacle to receive at least part of the patient's uterine cervix within the interior chamber;
  d. holding at least part of the patient's uterine cervix in the interior chamber; and
  e. pressing a pressure applying surface of the receptacle against the female patients vaginal fornix to occlude a uterine artery adjacent to the vaginal fornix.

22. The method of claim 21, wherein the uterine cervix is held in the interior chamber by applying a vacuum to the inner lumen of the elongated shaft in fluid communication with the interior chamber of the receptacle.

23. The method of claim 21, wherein a blood flow sensor is provided on a pressure applying surface of the cervical receptacle.

24. The method of claim 21, wherein said blood flow sensor comprises a Doppler ultrasound blood flow sensor.

25. The method of claim 21, further comprising detecting a change in blood flow in the uterine artery.

26. The method of claim 20, wherein the uterine artery remains occluded by pressure applied by the pressure applying surface of the cervical receptacle for a limited time.

27. The method of claim 26, wherein the limited time ranges from about 0.2 to about 24 hours.

28. The method of claim 26, wherein the limited time ranges from about 0.5 to about 16 hours.

29. An intravaginal uterine artery occlusion device, comprising:
  a. an elongated shaft which has a distal end, an inner lumen configured to be interconnected to a vacuum source and extending to the distal end;
  b. a cervical receptacle
    which is secured to the distal end of the elongated shaft,
    which has an open distal end,
    which has an interior chamber configured to receive at least part of a female patient's uterine cervix and having at least one groove in a wall thereof configured to be in fluid communication with the inner lumen in the shaft, and which has at least one extendable curtain secured to the open distal end of the receptacle with at least one pressure applying surface on a distal end of the extendable curtain to facilitate occlusion of the patient's uterine artery.

30. The intravaginal uterine artery occlusion device of claim 29, wherein the pressure applying surface comprises an occlusion bar.

31. The intravaginal uterine artery occlusion device of claim 30, wherein the occlusion bar is hydraulically operated to extend distal to the leading edge of the uterine cervix receptacle.

32. The intravaginal uterine artery occlusion device of claim 31, wherein the occlusion, bar has a pair of legs which extend from a surface of the occlusion bar opposite to the pressure applying surface thereof.

33. The intravaginal occlusion device of claim 32, wherein the pressure application member has a pair of arms with recesses therein configured to receive the legs extending from the occlusion bar.

34. The intravaginal occlusion device of claim 33, wherein at least one of the arm receiving recesses is a bore and is provided with a drive shaft slidably disposed therein configured to drive the received leg.

35. The intravaginal occlusion device of claim 34, wherein the drive shaft is driven by a first cylindrical member with one closed end secured to the proximal end of the drive shaft and one open end and a second cylindrical member with one open end which interfits with the open end of the first cylindrical member and one closed end with an aperture through which the drive shaft is slidably disposed.

36. The intravaginal occlusion device of claim 35, wherein the open ends of the first and second cylindrical members are thread ably engaged.

37. The intravaginal occlusion device of claim 36, wherein the open end of the first cylindrical member has a threaded exterior and the open end of the second cylindrical member has a threaded interior, whereby rotation of one of the cylindrical member with respect to the other cylindrical member adjusts the capacity of the fluid chamber.

38. The intravaginal occlusion device of claim 35, wherein drive shaft is slidably disposed within all elongated tubular member secured at a distal end to the pressure applying head and at a proximal end to the closed end of the second cylindrical member.

* * * * *